(12) United States Patent
Zustiak et al.

(10) Patent No.: US 10,725,382 B2
(45) Date of Patent: Jul. 28, 2020

(54) CUSTOM MULTIWELL PLATE DESIGN FOR RAPID ASSEMBLY OF PHOTO-PATTERNED HYDROGELS

(71) Applicant: Saint Louis University, St. Louis, MO (US)

(72) Inventors: Silviya Petrova Zustiak, St. Louis, MO (US); Naveed Zafar Ahmed, Lee's Summit, MO (US)

(73) Assignee: Saint Louis University, St. Louis, MO (US)

( * ) Notice: Subject to any disclaimer, the term of this patent is extended or adjusted under 35 U.S.C. 154(b) by 332 days.

(21) Appl. No.: 15/757,237

(22) PCT Filed: Sep. 2, 2016

(86) PCT No.: PCT/US2016/050191
§ 371 (c)(1),
(2) Date: Mar. 2, 2018

(87) PCT Pub. No.: WO2017/040989
PCT Pub. Date: Mar. 9, 2017

(65) Prior Publication Data
US 2018/0246411 A1   Aug. 30, 2018

Related U.S. Application Data

(60) Provisional application No. 62/214,593, filed on Sep. 4, 2015.

(51) Int. Cl.
*G03F 7/20* (2006.01)
*C12M 1/00* (2006.01)
(Continued)

(52) U.S. Cl.
CPC ........ *G03F 7/2012* (2013.01); *B01J 19/0046* (2013.01); *C12M 23/12* (2013.01);
(Continued)

(58) Field of Classification Search
CPC .......... B01J 19/0046; B01J 2219/00317; B01J 2219/00644; B01J 2219/00432;
(Continued)

(56) References Cited

U.S. PATENT DOCUMENTS 6,391,937 B1   5/2002 Beuhler et al.
6,699,665 B1   3/2004 Kim et al.
(Continued)

OTHER PUBLICATIONS

Syed et al., Simple Polyacrylaminde-based Multiwell Stiffness Assay for the study of stiffness-dependent cell Responses; JOVE; 2015, vol. 97, pp. 1-12.

*Primary Examiner* — John A McPherson
(74) *Attorney, Agent, or Firm* — Stinson LLP

(57) ABSTRACT

The present invention provides a system for conservation and efficient use of energy through controlling and monitoring of devices. At least one processing controller connected to a sensor and a device, the processing controller configured to receive the ambient data from the sensor and operating parameters from the device; a user module configured to IO receive input parameters from a plurality of users; a central processing module, connected to the structure, the user module, and the admin module through wired and/or wireless connection, the central processing module configured to process the data received from the processing controller adapted in the zone of the structure and generate the optimum parameters for operating the device adapted in the zone to the structure.

17 Claims, 10 Drawing Sheets

Specification includes a Sequence Listing.

(51) Int. Cl.
*B01J 19/00* (2006.01)
*G03F 7/038* (2006.01)
*C12M 1/32* (2006.01)
*C12M 1/12* (2006.01)
*G03F 1/22* (2012.01)
*G03F 7/027* (2006.01)
*G03F 7/26* (2006.01)
*B01L 3/00* (2006.01)

(52) U.S. Cl.
CPC ............ *C12M 23/20* (2013.01); *C12M 25/14* (2013.01); *G03F 1/22* (2013.01); *G03F 7/027* (2013.01); *G03F 7/038* (2013.01); *G03F 7/2004* (2013.01); *G03F 7/2014* (2013.01); *G03F 7/2045* (2013.01); *G03F 7/26* (2013.01); *B01J 2219/0072* (2013.01); *B01J 2219/00317* (2013.01); *B01J 2219/00432* (2013.01); *B01J 2219/00644* (2013.01); *B01J 2219/00711* (2013.01); *B01J 2219/00743* (2013.01); *B01L 3/5085* (2013.01); *C12N 2531/00* (2013.01); *C12N 2535/10* (2013.01); *C12N 2539/00* (2013.01)

(58) Field of Classification Search
CPC ...... C12M 23/12; C12M 23/20; C12M 25/14; C12N 2535/10; G03F 7/027; G03F 7/028; G03F 7/038; G03F 7/2004; G03F 7/2012; G03F 7/2014
USPC ........................................................ 430/320
See application file for complete search history.

(56) References Cited

U.S. PATENT DOCUMENTS

| | | | |
|---|---|---|---|
| 2003/0175824 A1* | 9/2003 | Pishko | B01L 3/5085 506/7 |
| 2004/0048392 A1 | 3/2004 | Kidd | |
| 2004/0191891 A1 | 9/2004 | Tsinberg et al. | |
| 2006/0188940 A1 | 8/2006 | Cima et al. | |
| 2011/0053270 A1 | 3/2011 | Chang et al. | |
| 2016/0038902 A1* | 2/2016 | Chao | B01J 19/0046 427/2.1 |
| 2016/0175800 A1* | 6/2016 | Murphy | B01J 19/0046 506/9 |

* cited by examiner

CUSTOM MULTIWELL PLATE DESIGN FOR RAPID ASSEMBLY OF PHOTO-PATTERNED HYDROGELS

CROSS REFERENCE TO RELATED APPLICATIONS

This application is a national phase application of PCT/US2016/050191, filed on Sep. 2, 2016, which claims priority to U.S. Provisional Application No. 62/214,593, filed on Sep. 4, 2015, each of which is hereby incorporated by reference in its entirety.

STATEMENT IN SUPPORT FOR FILING A SEQUENCE LISTING

A paper copy of the Sequence Listing and a computer readable form of the Sequence Listing containing the file named "SLU 15-012US_ST25.txt", which is 698 bytes in size (as measured in MICROSOFT WINDOWS® EXPLORER), are provided herein and are herein incorporated by reference. This Sequence Listing consists of SEQ ID NOs:1-2.

BACKGROUND OF THE DISCLOSURE

The present disclosure relates generally to biomaterial platforms. More particularly, the present disclosure is directed to a system and methods for preparing photo-patterned hydrogel-containing multiwell plate designs. The system and methods of the present disclosure provides a faster and more efficient assembly of photo-patterned hydrogel-containing multiwell plate designs.

Most tissues in the body are viscoelastic with a Young's modulus ranging from 0.1-100 kPa for soft tissues and in the MPa range (~2-20 MPa) for very stiff tissues such as bone and articular cartilage; yet, most in vitro cell research is conducted on tissue culture polystyrene (TCP) which has a modulus of ~1 GPa. To understand the implication of this stiffness mismatch, in the past two decades a growing body of research has been dedicated to elucidating the effect of substrate compliance on cell behavior. Various hydrogels spanning a wide range of stiffness have thus been developed to aid the deciphering of stiffness-dependent cell biology including polyacrylamide (PA), polyethylene glycol (PEG), polydimethyl siloxane (PDMS), and alginate. Much research involving stiffness modulated cell responses utilizes polyacrylamide (PA) gels which are readily available, inexpensive and simple to implement and, most importantly, can be prepared in a physiologically relevant range of Young's modulus, namely 0.3-300 kPa, encompassing both soft and some stiff tissues.

Currently, hydrogels are mostly prepared in small batches because the preparation protocols are time and labor intensive. Several groups have attempted to produce hydrogels for cell culture in a semi high-throughput format. Developed methods include cutting gels from a thick gel sheet, which is technically challenging for soft gels, cutting gels from a gel sheet pre-adhered to a flexible plastic support, which can accommodate gels of any stiffness, or sandwiching gel pre-cursor solution with a custom coverglass array directly into a well plate. While these methods allow for hydrogel assembly in a multiwell plate format that is not possible by traditional methods, the above techniques are still time consuming, labor intensive and technically challenging.

Accordingly, there exists a need for alternative systems and methods for preparing hydrogels for cell culture in a semi high-throughput format.

BRIEF DESCRIPTION OF THE DISCLOSURE

The present disclosure is generally directed to biomaterial platforms. More particularly, the present disclosure is directed to hydrogel-containing multiwell plate designs and methods for preparing hydrogel-containing multiwell plates.

In one aspect, the present disclosure is directed to a system for preparing a photo-patterned hydrogel-containing multiwell plate. The system comprises: a first assembly to prepare a plurality of photo-patterned hydrogels, the first assembly comprising: a first base; a flexible adhesive support in contact with the first base, the flexible adhesive support configured to receive a hydrogel precursor solution disposed thereon; a spacer, wherein the spacer forms a border at the first base edges of the first base; and a photomask comprising a plurality of apertures and configured to be removably positioned over the hydrogel precursor solution where upon exposure of the hydrogel precursor solution to a light source polymerizes the hydrogel precursor solution to prepare the plurality of photo-patterned hydrogels on the surface of the flexible adhesive support; and a second assembly to prepare a multiwell plate comprising a plurality of photo-patterned hydrogels, the second assembly comprising: an upper structure comprising a plurality of apertures configured to position each individual photo-patterned hydrogel on the surface of the flexible adhesive support within an aperture of the upper structure, wherein upon positioning each individual photo-patterned hydrogel on the surface of the flexible adhesive support within an aperture of the upper structure forms a well; a second base; and a fastener configured to fasten the upper structure, the flexible adhesive support and the second base, wherein upon fastening the upper structure, the flexible adhesive support and the second base forms the photo-patterned hydrogel-containing multiwell plate.

In another aspect, the present disclosure is directed to a system for preparing a photo-patterned hydrogel-containing multiwell plate. The system comprises: a first assembly configured to prepare a plurality of photo-patterned hydrogels, the first assembly comprising: a base configured to receive a hydrogel precursor solution disposed thereon; a spacer, wherein the spacer forms a border at the base edges of the base; and a photomask comprising a plurality of apertures and configured to be removably positioned over the hydrogel precursor solution where upon exposure of the hydrogel precursor solution to a light source polymerizes the hydrogel precursor solution to prepare the plurality of photo-patterned hydrogels on the surface of the base; and a second assembly configured to prepare a multiwell plate comprising a plurality of photo-patterned hydrogels, the second assembly comprising: an upper structure comprising a plurality of apertures configured to position each individual photo-patterned hydrogel on the surface of the base within an aperture of the upper structure, wherein upon positioning each individual photo-patterned hydrogel on the surface of the base within an aperture of the upper structure forms a well; and a fastener configured to fasten the upper structure and the base, wherein upon fastening the upper structure and the base forms the photo-patterned hydrogel-containing multiwell plate.

In another aspect, the present disclosure is directed to a method for preparing a photo-patterned hydrogel-containing multiwell plate. The method comprises assembling a first assembly to prepare a plurality of photo-patterned hydrogels, the first assembly comprising: a first base; a flexible adhesive support in contact with the first base, the flexible adhesive support configured to receive a hydrogel precursor solution disposed thereon; a spacer, wherein the spacer forms a border at the first base edges of the first base; applying a hydrogel precursor solution to an upper surface of the flexible adhesive support; positioning a photomask over the hydrogel precursor solution; exposing the first assembly to a light source for a sufficient time to polymerize the hydrogel precursor solution exposed to the light source to prepare a flexible adhesive support comprising a plurality of photo-patterned hydrogels; disassembling the first assembly; and assembling a second assembly to prepare a multiwell plate comprising a plurality of photo-patterned hydrogels by positioning each individual photo-patterned hydrogel on the upper surface of the flexible adhesive support within an aperture of an upper structure wherein the upper structure comprises a plurality of apertures, wherein upon positioning each individual photo-patterned hydrogel on the surface of the flexible adhesive support within an aperture of the upper structure forms a well; positioning an upper surface of a second base in contact with a bottom surface of the flexible adhesive support; and fastening the base, the flexible adhesive support and the upper structure with a fastener to assemble the second assembly, wherein upon assembly of the second assembly prepares the multiwell plate comprising a plurality of photo-patterned hydrogels.

In another aspect, the present disclosure is directed to a method for preparing a photo-patterned hydrogel-containing multiwell plate, the method comprising: assembling a first assembly configured to prepare a plurality of photo-patterned hydrogels, the first assembly comprising: a base configured to receive a hydrogel precursor solution disposed thereon; a spacer, wherein the spacer forms a border at the base edges of the base; applying a hydrogel precursor solution to an upper surface of the base; positioning a photomask comprising a plurality of apertures over the hydrogel precursor solution; exposing the first assembly to a light source for a sufficient time to polymerize the hydrogel precursor solution exposed to the light source to prepare a plurality of photo-patterned hydrogels on the upper surface of the base; disassembling the first assembly; and assembling a second assembly to prepare a multiwell plate comprising a plurality of photo-patterned hydrogels by positioning each individual photo-patterned hydrogel on the upper surface of the base within an aperture of an upper structure wherein the upper structure comprises a plurality of apertures; and fastening the base and the upper structure with a fastener to assemble the second assembly, wherein upon assembly of the second assembly prepares the multiwell plate comprising a plurality of photo-patterned hydrogels.

In accordance with the present disclosure, devices and methods have been discovered that surprisingly allow for the rapid assembly of photo-patterned photopolymerizable hydrogels in multiwell plate formats. The methods of the present disclosure have a broad and significant impact, as they allow for the preparation of biomaterial platforms that exhibit a wide range of stiffness and are available in a semi-high-throughput format such as a multiwell plate that are useful for elucidating cell-substrate relationships. Such devices can have an immediate impact in research areas such as, for example, drug screening, where high-throughput is a critical requirement. This is not possible with traditional methods that can take up to 2 days to prepare gel-containing multiwell plates due to long waiting times between steps and result in non-uniform gels contained within each well of the multiwell plates prepared using traditional methods.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 3A is an isometric view of the bottom of the upper structure showing representative dimensions. FIG. 3B is a side view of the upper structure showing representative dimensions. FIG. 3C is a front view of the upper structure showing representative dimensions. FIG. 3D is an isometric view of the top of the upper structure.

FIG. 7A is a top view photographic image of a second assembly. FIG. 7B is a bottom view photographic image of a second assembly. FIG. 7C is a side view photographic image of a second assembly.

Figure 1:
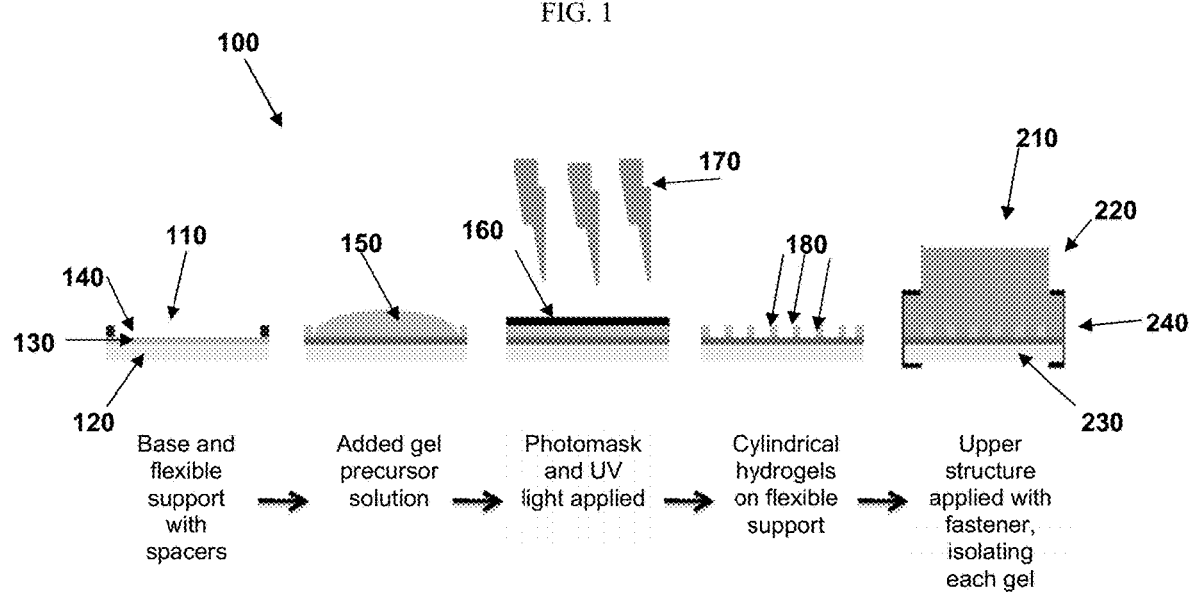
FIG. 1 is schematic representation illustrating an embodiment of the system and a method for preparing a photo-patterned hydrogel-containing multiwell plate.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, a custom multiwell plate design that allows for a single-step hydrogel stiffness assay assembly that reduces preparation time and labor intensity by several fold. Hydrogel stiffness is controlled by light intensity and exposure time to achieve a wide stiffness range from a single hydrogel precursor solution. The geometry of the individual hydrogels can be defined by a photomask and hydrogel thickness can be controlled by spacers. The multiwell plate exhibits proper gas exchange, minimum evaporation, and allows for cell growth and proliferation profiles comparable to standard multiwell plates.

System

In one aspect, the present disclosure is directed to a system for preparing a photo-patterned hydrogel-containing multiwell plate. The system comprises: a first assembly to prepare a plurality of photo-patterned hydrogels, the first assembly comprising: a first base; a flexible adhesive support in contact with the first base, the flexible adhesive support configured to receive a hydrogel precursor solution disposed thereon; a spacer, wherein the spacer forms a border at the first base edges of the first base; and a photomask comprising a plurality of apertures and configured to be removably positioned over the hydrogel precursor solution where upon exposure of the hydrogel precursor solution to a light source polymerizes the hydrogel precursor solution to prepare the plurality of photo-patterned hydrogels on the surface of the flexible adhesive support; and a second assembly to prepare a multiwell plate comprising a plurality of photo-patterned hydrogels, the second assembly comprising: an upper structure comprising a plurality of apertures configured to position each individual photo-patterned hydrogel on the surface of the flexible adhesive support within an aperture of the upper structure, wherein upon positioning each individual photo-patterned hydrogel on the surface of the flexible adhesive support within an aperture of the upper structure forms a well; a second base; and a fastener configured to fasten the upper structure, the flexible adhesive support and the second base, wherein upon fastening the upper structure, the flexible adhesive support and the second base forms the photo-patterned hydrogel-containing multiwell plate. The system can optionally include a seal configured to seal the well formed upon assembly of the upper structure, the flexible adhesive support and the base. The system can optionally include a lid.

Referring to FIG. 1 depicting an illustration of an exemplary system, the system 100 includes a first assembly 110. The first assembly 110 includes a base 120, a flexible adhesive support 130, and spacers 140. During hydrogel preparation, a hydrogel precursor solution 150 is applied to the upper surface of the flexible adhesive support 130. A photomask 160 is placed over the hydrogel precursor solution 150 and exposed to a light source 170. After light exposure, the photomask 160 and spacers 140 are removed revealing a plurality of photo-patterned hydrogels 180 on the upper surface of the flexible adhesive support 130.

Figure 2:
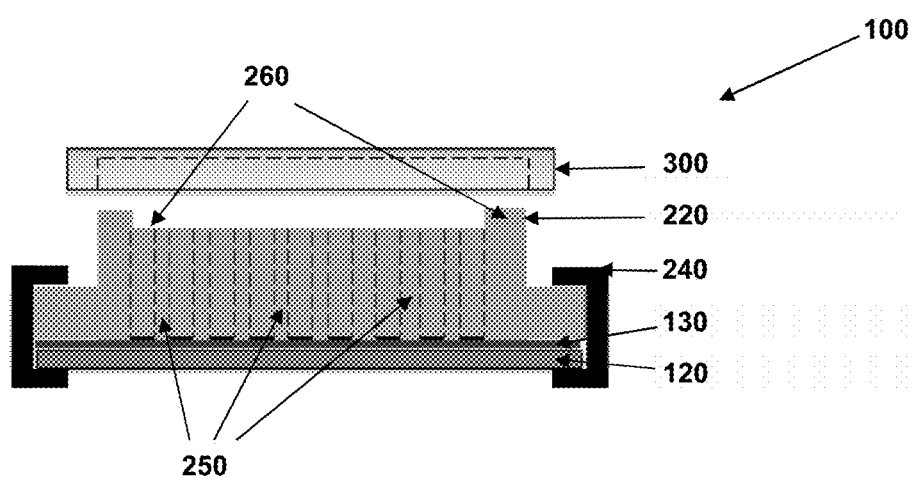
FIG. 2 is side view of a schematic representation of a second assembly of the system.
Figure 3A:
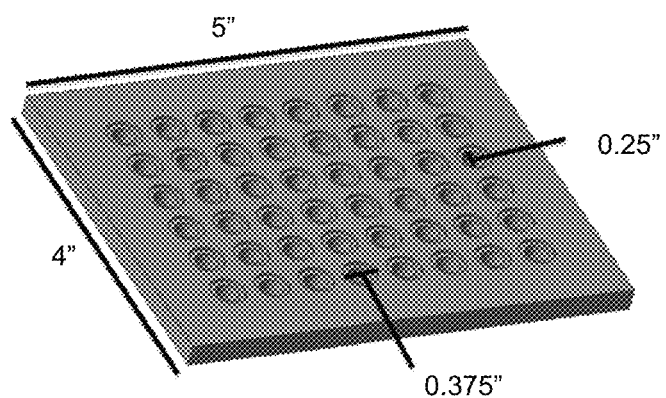
FIGS. 3A-3D are isometric views of an upper structure.
Figure 3B:
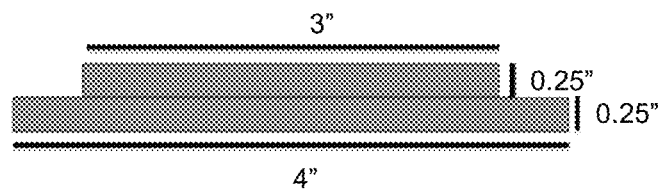
Figure 3C:
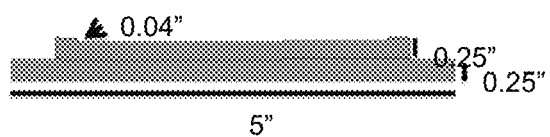
Figure 3D:
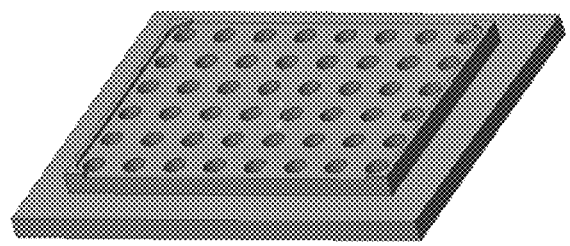
Figures 7A, 7B, 7C:
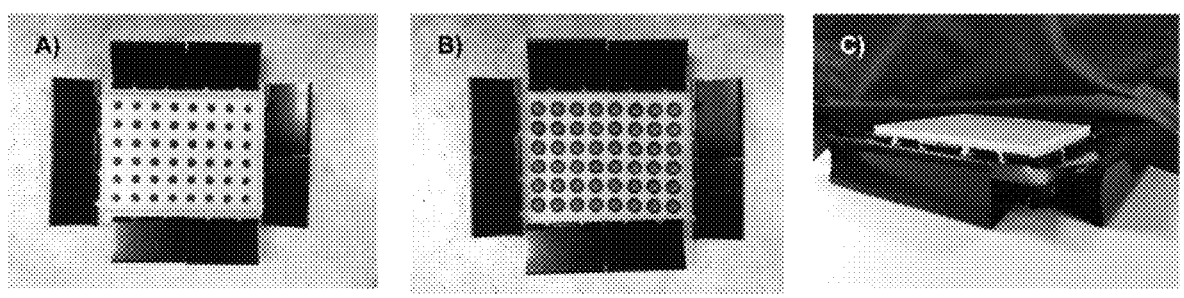
FIG. 7A-7C are photographic images of an assembled second assembly of the system.

When the second assembly 210 of the system 100 is assembled, the flexible adhesive support 130 having plurality of photo-patterned hydrogels 180 is fit together with the upper structure 220 such that individual hydrogels of the flexible adhesive support 130 are positioned within individual apertures (i.e., through-holes) of the upper structure 220, which results in the formation of wells 250 wherein the bottom of each well includes a hydrogel (see, FIG. 2). Thus upon positioning, the hydrogel of the flexible adhesive support forms the bottom surface of the well and the aperture walls of the upper structure form the side walls of the well (FIG. 2). A base 230 is positioned in contact with the bottom surface of the flexible adhesive support 130 to provide a more rigid structure to support the flexible adhesive support. Notably, the first base 120 of the first assembly 110 can be re-used as the second base 230 of the second assembly 210 once the spacers 140 are removed. The base 230, upper structure 220 and flexible adhesive support 130 are held together using a fastener 240. The components of the second assembly 210 can be fastened together with any suitable fastener such as, for example, binder clips and clamps. An optional seal (not illustrated) can be positioned between a bottom surface of the upper structure 220 and the top surface flexible adhesive support 130. FIGS. 7A-7C are photographic images of a representative final assembled second assembly 210.

The optional seal (not illustrated) contacts the top surface of the flexible adhesive support 130 and the bottom surface of the upper structure 220 to prevent leaking. Any material can be used to form a seal between the top surface of the flexible adhesive support 130 and the bottom surface of the upper structure 220 to prevent leaking when the flexible adhesive support 130 and upper structure 220 are assembled. When the apertures (i.e., through-holes) of the upper structure are cylindrical in shape, a particularly suitable seal can be o-rings (such as silicon o-rings). A single o-ring is placed at the bottom surface of the upper structure 220 to surround the aperture. The bottom surface of the upper structure 220 surrounding each aperture can contain a groove in which the o-ring can be positioned. In another embodiment, a seal can be made of a flexible sealing material such as a silicone sheet that includes apertures (i.e., through-holes) matching the pattern of the photo-pattern hydrogels such that individual hydrogels are positioned through the apertures of the flexible sealing material. Although less desirable, it is possible to assemble the second assembly 210 of the system 100 without using a seal between the flexible adhesive support 130 and the upper structure 220.

The upper structure can have overall dimensions and well volumes similar to a standard 6-well, 12-well, 24-well, 48-well, 96-well and 384-well plates.

Any material suitable material can be used to make the base. Particularly suitable materials for each component are biocompatible materials of desired mechanical and physical properties. A particularly suitable material for making the base is glass. The base can be any desired shape. A particularly suitable shape is rectangular, which is similar to a standard multiwell plate. The base can be any desired dimension. For a rectangular embodiment, particularly suitable dimensions (width×length×height) can be 4 inches×5 inches×0.25 inches. The width and length of the base can be designed to be similar to the base of a standard multiwell plate. The height of the base should be such that buckling of the base is avoided. Buckling is particularly undesirable because it can cause fracture of the base due to increased stress and can compromise the seal with the upper structure resulting in leakage. As illustrated in FIG. 1, the base 120 of the first assembly 110 can also be used as the second base 230 of the second assembly 210 once the spacers 140 are removed. If desired, however, the base 120 of the first assembly 110 and the second base 230 of the second assembly 210 can be distinct.

Particularly suitable flexible adhesive supports desirably have two surfaces—a hydrophobic surface that repels the hydrogel and a hydrophilic surface to which the hydrogel adheres. When assembled, the flexible adhesive support 130 is positioned onto the base 120 with the hydrophobic surface of the flexible adhesive support 130 is in contact with the top (or upper) surface of the base 120. In a particularly suitable embodiment, the hydrogel is covalently coupled to the hydrophilic surface of the flexible adhesive support. A particularly suitable flexible adhesive support material is GELBOND® (commercially available from Lonza, Allendale, N.J.). Advantageously, the use of the flexible adhesive support is disposable, enables hydrogels to permanently adhere upon polymerization thus anchoring the hydrogel to the bottom of the well upon assembly with the second assembly of the system, and allows easy handling when the first assembly of the system is disassembled following preparation of the photo-patterned hydrogel on the surface of the flexible adhesive support. Handling of the hydrogel on the flexible adhesive support independently of the system also permits easy cell fixation and processing such as staining, immunocytochemistry and imaging. The flexible adhesive support also allows for simple clean-up and multiple reuse of the system.

The upper structure 220 of the second assembly 210 includes apertures (i.e., through-holes) that form wells upon assembly of the second assembly and isolate each hydrogel. When assembled, the groove with o-rings seals the contents of each well. The upper structure can also include a lip 260 on two sides of the middle that separates the upper structure from the lid and allows for gas exchange. Any suitable material can be used for preparing the upper structure. Preferably, the material is easily machined, has the desired mechanical properties (1 GPa) to prevent buckling and/or indentation by the fasteners, and is biocompatible. A particularly suitable material for the upper structure is high-density polyethylene (HDPE). The thickness of the upper structure can be varied.

Dimensions of a representative embodiment of an upper structure having cylindrical apertures are depicted in FIG. 3. The bottom length and width can be designed to match that of the base. For the representative embodiment depicted in FIG. 3, an additional 0.5" on each side have a thickness of 0.25" to accommodate the fasteners upon design assembly. The middle of the piece (coming in further than 0.5" from the edge) is 0.46". The representative embodiment also includes a lip on two sides of the middle that rises 0.04". Apertures of the upper structure can be any desirable shape. A particularly suitable shape is cylindrical as illustrated in FIGS. 3A & 3D.

Figure 5:
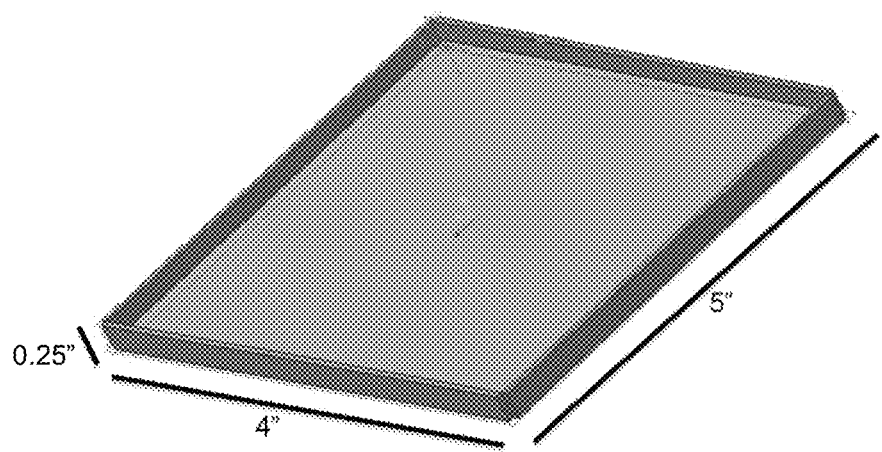
FIG. 5 is an isometric view of a lid showing representative dimensions.

Referring to FIG. 2, the system 100 can include a lid 300. Suitable material for preparing the lid is a clear acrylic plastic with HDPE sides (FIG. 5). The exemplary lid illustrated in FIG. 5 has the following dimensions: 3.375"×4.5"× 0.06". The dimensions of the lid are larger than the area of the raised portion of the upper structure (3"×4") to allow for proper gas exchange. The HDPE sides are adhered to the side of the lid using quick-drying adhesive (e.g., super glue commercially available from Loctite, Westlake, Ohio).

If desired, system components can be sterilized. As known by those skilled in the art, different sterilization procedures can be used for each device component as dictated by the component properties, geometry and opacity. For example, in embodiments using a glass base, which is transparent, the base can be sterilized by wiping with 70% ethanol followed by a 30 min UV exposure (302 nm). In embodiments using o-rings as the seal, the o-ring seals can be sterilized by soaking in 70% ethanol and rinsed to remove residual ethanol. The upper structure can similarly be sterilized by soaking in 70% ethanol and rinsed to remove residual ethanol. The hydrogels and the flexible plastic support can be sterilized by UV exposure (302 nm).

Suitably, cells can be seeded on the surface of the individual hydrogels. Alternatively, cells can be seeded within the individual hydrogels by including cells within a hydrogel precursor solution and exposure to a light source results in the encapsulation of cells within the hydrogels. As known to those skilled in the art, any cell type can be seeded onto or within the individual hydrogels. Cell types that can be used include, for example, epithelial cells, endothelial cells, macrophages, stem cells (e.g., adipose-derived stem cells, mesenchymal stem cells, embryonic stem cells), fibroblasts (e.g., ligament fibroblasts, tendon fibroblasts, muscle fibroblasts, dermal fibroblasts), muscle cells (e.g., skeletal muscle cells, cardiac muscle cells, smooth muscle cells), liver cells, neuronal cells, bone cells (e.g., osteoblasts), lung cells, cancer cells and combinations thereof.

Hydrogels can further incorporate a cell adhesion molecule. The cell adhesion molecule can be, for example, fibronectin, fibrinogen, vitronectin, collagen, laminin, short adhesive peptide ligands such as RGD (arginine-glycine-aspartic acid) peptide, LDV (leucine-aspartic acid-valine) peptide, IKVAV (isoleucine-lysine-valine-alanine-valine; SEQ ID NO:1) peptide, YIGSR (tyrosine-isoleucine-glycine-serine-arginine; SEQ ID NO:2) peptide, and combinations thereof. Incorporation of cell adhesion molecules can induce favorable cell to extracellular matrix interactions, promote in vivo-like three-dimensional adhesion and activate cell signaling pathways, maintain cell phenotype, and support cell differentiation.

In another aspect, the hydrogels can include other biomolecules such as, for example, recombinant and chemically synthesized proteins and peptides and nucleic acids (DNA and RNA). Suitable biomolecules can be, for example, growth factors, cytokines, bioactive lipids, immunoglobulins, and combinations thereof. Particularly suitable biomolecules can be, for example, platelet derived growth factor (PDGF), transforming growth factor beta (TGFβ), vascular endothelial growth factor (VEGF), fibroblast growth factor (FGF), epidermal growth factor (EGF), human growth factor (HGF), nerve growth factor (NGF), bone morphogenetic proteins (BMPs), insulin-like growth factors (e.g., IGF-1 and IGF-2), keratinocyte growth factor, connective tissue growth factor, chemotactic proteins, sphingosine 1-phosphate (S1P), various macrophage and monocyte mediators such as RANTES (Regulated upon Activation, Normal T-cell Expressed, and Secreted), tumor necrosis factor α (TNF α), interferon gamma (IFNγ), and granulocyte-macrophage colony stimulating factor (GM-CSF), lipoxin and combinations thereof. Suitable cytokines can be, for example, interleukins (e.g., IL-1-IL-36) and interferons (e.g., interferon type I, interferon type II, interferon type III).

In another embodiment, the present disclosure is directed to a system for preparing a photo-patterned hydrogel-containing multiwell plate. The system includes: a first assembly configured to prepare a plurality of photo-patterned hydrogels, the first assembly comprising: a base configured to receive a hydrogel precursor solution disposed thereon; a spacer, wherein the spacer forms a border at the base edges of the base; and a photomask comprising a plurality of apertures and configured to be removably positioned over the hydrogel precursor solution where upon exposure of the hydrogel precursor solution to a light source polymerizes the hydrogel precursor solution to prepare the plurality of photo-patterned hydrogels on the surface of the base; and a second assembly configured to prepare a multiwell plate comprising a plurality of photo-patterned hydrogels, the second assembly comprising: an upper structure comprising a plurality of apertures configured to position each individual photo-patterned hydrogel on the surface of the base within an aperture of the upper structure, wherein upon positioning each individual photo-patterned hydrogel on the surface of the base within an aperture of the upper structure forms a well; and a fastener configured to fasten the upper structure and the base, wherein upon fastening the upper structure and the base forms the photo-patterned hydrogel-containing multiwell plate.

In another embodiment, the present disclosure is directed to a system for preparing a photo-patterned hydrogel-containing multiwell plate. The system includes: a first assembly configured to prepare a plurality of photo-patterned hydrogels, the first assembly comprising: a base configured to receive a hydrogel precursor solution disposed thereon; and a photomask comprising a plurality of apertures configured to be positioned over the hydrogel precursor solution where upon exposure of the hydrogel precursor solution to a light source polymerizes the hydrogel precursor solution to prepare the plurality of photo-patterned hydrogels on the surface of the base; and a second assembly configured to prepare a multiwell plate comprising a plurality of photo-patterned hydrogels, the second assembly comprising: an upper structure comprising a plurality of apertures configured to position each individual photo-patterned hydrogel on the surface of the base within an aperture of the upper structure forms a well; and a fastener configured to fasten the upper structure and the base, wherein upon fastening the upper structure and the base forms the photo-patterned hydrogel-containing multiwell plate.

The base of the first assembly desirably is pre-treated with a solution to create a hydrophilic surface on the base to which the hydrogel adheres upon polymerization. A particularly suitable solution for pre-treating the base is Bind-Silane (γ-methacryloxypropyltrimethoxysilane) (commercially available from Sigma-Aldrich, St. Louis, Mo.).

Components of the first assembly (e.g., the base, the photomask and the hydrogel precursor solution) and components of the second assembly (e.g., the upper structure and the fastener) are described herein above. Optional components such as seals and lids are described herein above.

In another aspect, the present disclosure is directed to a method for preparing a photo-patterned hydrogel-containing multiwell plate. The method comprises assembling a first assembly to prepare a plurality of photo-patterned hydrogels, the first assembly comprising: a first base; a flexible adhesive support in contact with the first base, the flexible adhesive support configured to receive a hydrogel precursor solution disposed thereon; a spacer, wherein the spacer forms a border at the first base edges of the first base; applying a hydrogel precursor solution to an upper surface of the flexible adhesive support; positioning a photomask over the hydrogel precursor solution; exposing the first assembly to a light source for a sufficient time to polymerize the hydrogel precursor solution exposed to the light source to prepare a flexible adhesive support comprising a plurality of photo-patterned hydrogels; disassembling the first assembly; and assembling a second assembly to prepare a multiwell plate comprising a plurality of photo-patterned hydrogels by positioning each individual photo-patterned hydrogel on the upper surface of the flexible adhesive support within an aperture of an upper structure wherein the upper structure comprises a plurality of apertures, wherein upon positioning each individual photo-patterned hydrogel on the surface of the flexible adhesive support within an aperture of the upper structure forms a well; positioning an upper surface of a second base in contact with a bottom surface of the flexible adhesive support; and fastening the base, the flexible adhesive support and the upper structure with a fastener to assemble the second assembly, wherein upon assembly of the second assembly prepares the multiwell plate comprising a plurality of photo-patterned hydrogels.

In another embodiment, the present disclosure is directed to a method for preparing a photo-patterned hydrogel-containing multiwell plate, the method comprising: assembling a first assembly configured to prepare a plurality of photo-patterned hydrogels, the first assembly comprising: a base configured to receive a hydrogel precursor solution disposed thereon; a spacer, wherein the spacer forms a border at the base edges of the base; applying a hydrogel precursor solution to an upper surface of the base; positioning a photomask comprising a plurality of apertures over the hydrogel precursor solution; exposing the first assembly to a light source for a sufficient time to polymerize the hydrogel precursor solution exposed to the light source to prepare a plurality of photo-patterned hydrogels on the upper surface of the base; disassembling the first assembly; and assembling a second assembly to prepare a multiwell plate comprising a plurality of photo-patterned hydrogels by positioning each individual photo-patterned hydrogel on the upper surface of the base within an aperture of an upper structure wherein the upper structure comprises a plurality of apertures; and fastening the base and the upper structure with a fastener to assemble the second assembly, wherein upon assembly of the second assembly prepares the multiwell plate comprising a plurality of photo-patterned hydrogels.

In another embodiment, the present disclosure is directed to a method for preparing a photo-patterned hydrogel-containing multiwell plate, the method comprising: assembling a first assembly configured to prepare a plurality of photo-patterned hydrogels, the first assembly comprising: a base configured to receive a hydrogel precursor solution disposed thereon; applying a hydrogel precursor solution to an upper surface of the base; positioning a photomask comprising a plurality of apertures over the hydrogel precursor solution; exposing the first assembly to a light source for a sufficient time to polymerize the hydrogel precursor solution exposed to the light source to prepare a plurality of photo-patterned hydrogels on the upper surface of the base; disassembling the first assembly; and assembling a second assembly to prepare a multiwell plate comprising a plurality of photo-patterned hydrogels by positioning each individual photo-patterned hydrogel on the upper surface of the base within an aperture of an upper structure wherein the upper structure comprises a plurality of apertures; and fastening the base and the upper structure with a fastener to assemble the second assembly, wherein upon assembly of the second assembly prepares the multiwell plate comprising a plurality of photo-patterned hydrogels.

Initially, a hydrogel precursor solution is prepared. The hydrogel precursor solution includes a polymeric material and de-ionized water at a desired ratio to provide the overall stiffness of the gel. The hydrogel precursor solution can further include a photoinitiator. The precursor solution can optionally be degassed prior to gelation (i.e., polymerization). The hydrogel precursor solution is then applied to the hydrophilic side of the flexible adhesive support between spacers that are placed at the edges of the flexible plastic support (see, FIG. 1). The spacers maintain the hydrogel precursor solution on the flexible plastic support and also determines the hydrogel thickness. The hydrogel precursor solution can further include cells, cell adhesion molecules, and biomolecules, as described herein.

To polymerize and photo-pattern the hydrogel to match the apertures of the upper structure, a photomask (see, FIG. 4 for a representative embodiment of a photomask having circular cut-outs for preparing cylindrical hydrogels) is positioned on the spacers directly over the hydrogel precursor solution, which is then exposed to a light source to initiate crosslinking (see, FIG. 1). Any suitable photomask as known to those skilled in the art can be used and are commercially available. For example, a polyester mylar photomask can be ordered from CAD Arts Services Inc. (Bandon, Oreg.).

Figure 6:
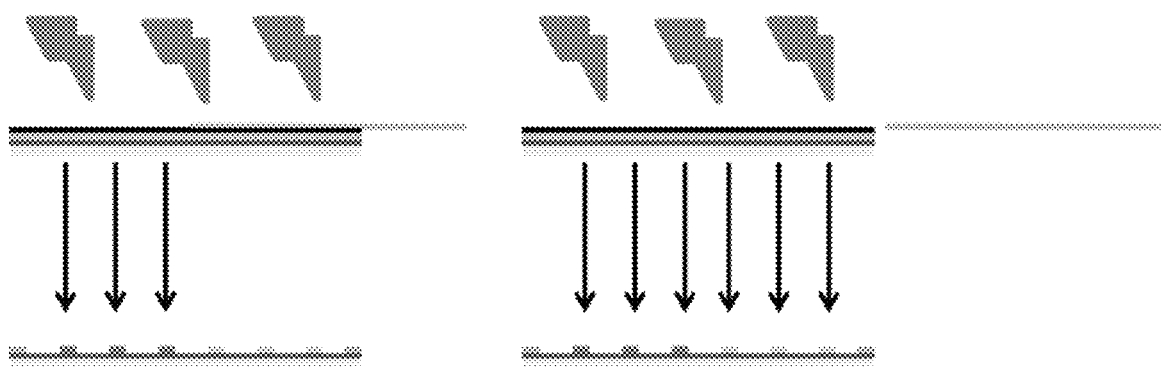
FIG. 6 is a schematic illustrating the process of cross-linking of the hydrogels by exposure to a light source to prepare photo-patterned hydrogels of varying stiffness using a single hydrogel precursor solution.

The method can further include exposing the hydrogel precursor solution to light for different times and/or different light intensities to prepare a photo-patterned hydrogel-containing multiwell plate wherein the photo-patterned hydrogel includes hydrogels with varying stiffness. Suitable stiffness can range from about 0.1 kPa to about 20 MPa. To achieve varying stiffness using a single hydrogel precursor solution, different parts of the precursor solution are exposed to light for different amounts of time and/or different light intensity. This is accomplished by positioning an opaque shield over the photomask intended for shorter exposure times and then moving the shield in step increments at pre-determined times (see, FIG. 6). Any opaque shield is suitable such as, for example, aluminum foil. The opaque shield selectively blocks light. A longer exposure time and/or higher light intensity will result in a stiffer gel (as depicted by the darker gray circles in FIG. 6). Conversely, a shorter exposure time and/or lower light intensity will result in a weaker gel. As the opaque shield is moved, parts of the gel are exposed to light for longer periods of time and/or higher light intensity, resulting in higher stiffness than the gels that were exposed to light for a shorter time and/or a lower light intensity. This creates the varying stiffness across the plate. After formation of the hydrogel by cross-linking, the photomask is removed and the excess un-crosslinked hydrogel precursor solution is rinsed away to result in hydrogels adhered to the flexible support in a pattern (see, FIG. 1). The hydrogels are then fit (i.e., positioned) into the apertures (i.e., through-holes) of the upper structure, which isolates each hydrogel (see, FIG. 1) and forms wells (as illustrated, for example, in FIG. 2 reference numeral 250).

Any hydrogel forming photopolymerizable polymeric material is suitable for use in the present disclosure. Particularly suitable hydrogel forming photopolymerizable polymeric materials can be acrylamide, acrylate derivatives of polyethylene glycol, methacrylate derivatives of polyethylene glycol, polyvinyl alcohol derivatives, polysaccharide derivatives such as methacrylated hyaluronic acid, dextran acrylate or methacrylate, collagen derivatives, fibrinogen derivatives, fibronectin derivatives, laminin derivatives, poly(propylene fumarate-co-ethylene glycol), methacrylated or acrylated poly(ethylene glycol)-co-poly(lactic acid), poly(ethylene glycol)-co-poly(alpha hydroxyl acid) diacrylate, polyethylene glycol-norborene, polyethylene glycol-oligoglycolyl-acrylates, methacrylated or acrylated gelatin, alginate or agarose, chitosan, co-polymers thereof, other methacrylate, acrylate, norborene or thiol-ene photopolymerizable hydrogels or interpenetrating networks, and combinations thereof. As understood by those skilled in the art, hydrogels are a water-swollen, and cross-linked polymeric network produced by the reaction of one or more monomers. The hydrogels can be homopolymeric hydrogels (i.e., a polymer network derived from a single species of monomer), copolymeric hydrogels (i.e., comprised of two or more different monomer species), and multipolymer interpenetrating polymeric hydrogels (i.e., comprised of two independent cross-linked synthetic and/or natural polymer component, contained in a network form).

Any multifunctional cross-linking agent that is compatible with the polymeric material is suitable for use in the present disclosure. Particularly suitable multifunctional cross-linking agents can be, for example, bis-acrylamide, trimethylol propane trimethacrylate, trimethylol propane triacrylate, pentaerythritol tetraacrylate, dipentaerythritol monohydroxy pentaacrylate, polyethylene glycol diacrylate, methyl methacrylate, and combinations thereof.

Any photoinitiator that is compatible with the polymeric material and cross-linking agent is suitable for use in the present disclosure. Particularly suitable photoinitiators can be, for example, α-hydroxyketones, phenylglyoxylates, benzyldimethyl-ketals, α-aminoketones, mono acyl phosphines, bis acyl phosphines, phosphine oxides, metallocenes, iodonium salts, Irgacure, riboflavin and camphorquinone.

As known by those skilled in the art, photoinitiation can be achieved by visible, UV, infra-red and near infra-red light at various intensities, where polymerization time would be dependent on the light intensity, the duration of exposure, and the distance of the sample from the light source. Suitable visible light for polymerization can be 8 mW/cm$^2$, 400-500 nm (Novacure collimated light source). Suitable UV light for polymerization can be 15 mW/cm$^2$, 365 nm as provided by commercially available UV lamps (e.g., IntelliRay 600, UviTron, West Springfield, Mass.).

Hydrogels can further include extracellular matrix protein coatings. Suitable extracellular matrix protein coatings can be, for example, collagens, fibronectins, laminins, fibronectins, elastins and combinations thereof. To apply the extracellular matrix protein coating, the hydrogels are derivatized with a crosslinker to create reactive groups on the hydrogel. For example, hydrogels can be derivatized with Sulfo-SANPAH (commercially available from Thermo Scientific; Redford, Ill.) dissolved in dimethyl sulfoxide (DMSO):de-ionized water at a ratio of 4:96. The crosslinker solution is placed on top of each hydrogel and activated by exposure to high intensity UV light. Unreacted crosslinker can be removed by rinsing. The extracellular matrix protein coating solution is then added on top of the hydrogel in each well and allowed to react. The unreacted extracellular matrix protein coating solution can be removed by rinsing. The coated hydrogels can optionally be sterilized (e.g., under UV (~302 nm)). A sterilization step can be omitted if sterile crosslinker and extracellular matrix protein solutions are used for the coating steps.

The disclosure will be more fully understood upon consideration of the following non-limiting Examples.

Example 1

In this Example, components, photopatterning, and assembly of an exemplary system is described.

A glass base in a rectangular shape with dimensions of 4"×5"×0.25" was purchased (Gate City Glass & Co Inc., Kansas City, Mo.). The width and length were designed to be similar to the base of a standard multiwell plate and the height was chosen such that buckling of the base was negligible. The glass base was lined with a GelBond flexible plastic support (GELBOND®, commercially available from Lonza). The GELBOND® flexible plastic support was positioned onto the glass base hydrophobic side-down.

An upper structure was prepared from high-density polyethylene (HDPE). The dimensions of the exemplary upper structure are depicted in FIG. 3. The bottom length and width were constructed to match that of the glass base, namely 4"×5". The upper structure included an additional 0.5" on each side having a thickness of 0.25" to accommodate the clamps for assembly of the device. The middle of the piece (coming in further than 0.5" from the edge) was 0.46". A lip on two sides of the middle of the upper structure rises 0.04" to separate the upper structure from the plate lid for proper gas exchange. On the bottom of the upper structure, a circular groove, ⅛" in diameter and ¹⁄₃₂" deep, surrounds each well. The groove houses silicone o-rings (commercially available from Sealing Devices Inc., Lancaster, N.Y.) to seal the contents of each well.

Figure 4:
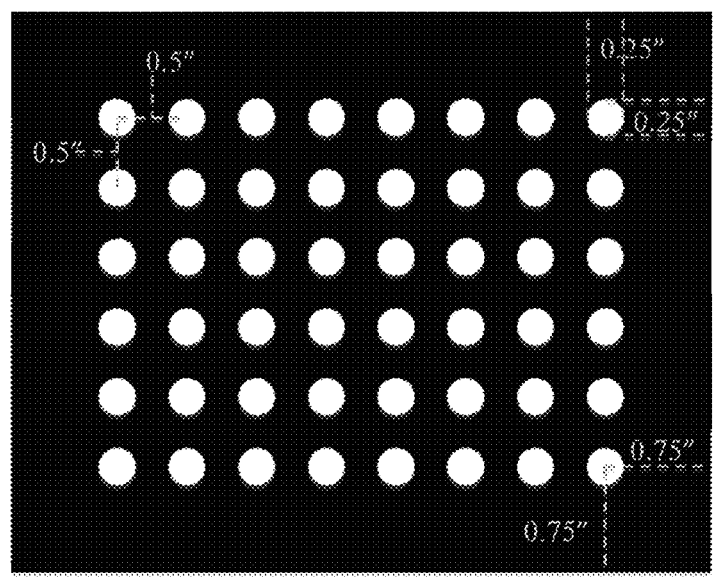
FIG. 4 is a schematic illustration of a photomask showing representative dimensions.

As depicted in FIG. 4, a photomask prepared from polyester mylar was custom ordered from CAD Arts Services Inc. (Bandon, Oreg.).

A lid was made from a clear acrylic plastic with HDPE sides (see, FIG. 5). The acrylic piece had the following dimensions: 3.375"×4.5"×0.06". The dimensions of the lid were larger than the area of the raised portion of the upper structure (3"×4") to permit gas exchange. The HDPE sides (short side having dimensions of 3.25"×0.25"×0.06"; long side having dimensions of 4.25"×0.25"×0.6") were adhered to the side of the acrylic using quick-drying super glue (commercially available from Loctite, Westlake, Ohio).

A polyacrylamide (PA) gel precursor solution was prepared using acrylamide (40% w/v; Bio-Rad, Hercules, Calif.), bis-acrylamide (2% w/v; Bio-Rad, Hercules, Calif.) and de-ionized water at a desired ratio to determine the overall stiffness of the hydrogel. For example, for the data presented here, 12% acrylamide and 0.25% bis-acrylamide in de-ionized water were used. The PA gel precursor solution was degassed for 30 minutes prior to gelation. The photoinitiator Irgacure 2959 (BASF Corporation, Florham Park, N.J.)) was added to the solution at 0.1% w/v, mixed gently by pipetting up and down five times and pipetted onto the hydrophilic side of GELBOND® between spacers. Silicone spacers of 0.5 mm (Grace Bio-Labs, Bend, Oreg.), were placed around the edges of the GELBOND® to assure uniform hydrogel thickness. Approximately 10 ml of PA gel precursor solution was used.

The photomask was positioned on the spacers directly over the PA gel precursor solution. The solution was then exposed to UV light (IntelliRay 600, UviTron, West Springfield, Mass., 15 mW/cm$^2$, 365 nm) to initiate crosslinking. To achieve varying stiffness from the same precursor solution, different parts of the gel were exposed to UV light for different time periods. This was accomplished by positioning an aluminum foil opaque shield over the wells intended for shorter exposure times and then moving the shield in step increments at pre-determined times (see, FIG. 6): longer exposure times resulted in stiffer gels. After crosslinking, the photomask was removed and the excess un-crosslinked PA solution was rinsed away with de-ionized water leaving behind cylindrical hydrogels that were permanently adhered to the GELBOND®. Each cylindrical hydrogel was then fit to the apertures of the upper structure to form wells in the fully assembled device. The glass base and upper structure were then clamped together with eight binder clips (2" wide, 1" capacity; Officemate OIC, Edison, N.J.)—two clips on each side. An image of the final assembled device is depicted in FIG. 7.

For collagen coating, PA gels were coated with rat-tail Collagen Type I (BD BioSciences, Bedford, Mass.) at a concentration of 0.2 mg/ml in PBS to allow for cell adhesion. To apply the collagen coating, the gels were first derivatized with Sulfo-SANPAH (Thermo Scientific, Redford, Ill.) dissolved in dimethyl sulfoxide (DMSO):de-ionized water at a ratio of 4:96. To prepare the Sulfo-SANPAH solution, the reagent was first dissolved in DMSO at 10% w/v and stored at −80° C. in 20 µl aliquots until further use. Each aliquot was thawed and diluted in deionized water immediately before use. Approximately 50 µl of the Sulfo-SANPAH solution was placed on top of each gel and activated by exposure to high intensity UV light for 5 minutes. The unreacted crosslinker was removed by rinsing with PBS twice. Collagen solution was then added on top of each gel at ~50 µl per well and allowed to react for 2 hours at room temperature. The excess unreacted collagen was then rinsed with 10 mM PBS twice and sterilized under UV (~302 nm) in a tissue culture hood for 2 hours prior to cell seeding. The sterilization step can be omitted if sterile Sulfo-SANPAH and collagen solutions are used for the coating steps. Coated gels can be used immediately or stored hydrated at 4° C. for up to 2 days.

The results of all experiments are the mean values (±S.D.) of three to eight samples per condition, performed in two to six independent experiments. Comparisons between multiple samples were performed with single factor analysis of variance (ANOVA) and comparisons between two samples were performed with two-tailed Student's t-test, followed by post-hoc analysis.

Figure 8:
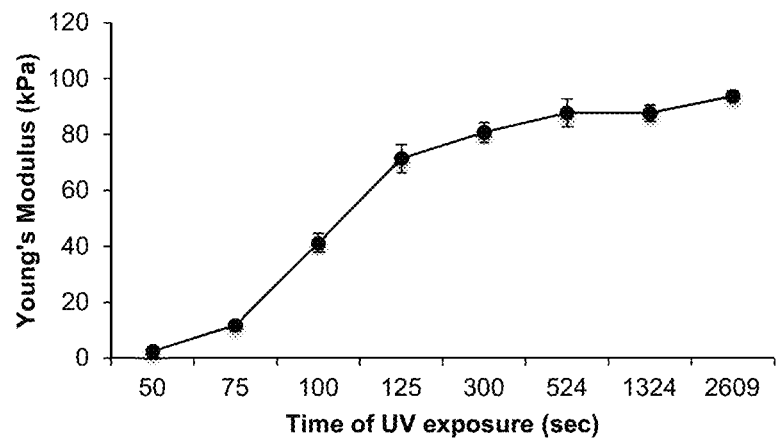
FIG. 8 is a graph depicting an increase in polyacrylamide gel stiffness upon increased exposure time to UV light.

As depicted in FIG. 8, the Young's modulus of a PA gel made from 12% acrylamide and 0.25% bis-acrylamide as a function of UV exposure time. The data indicates that ~10-fold difference in stiffness was achieved from a single PA gel precursor solution.

Example 2

For rheology testing, the gels were prepared in the form of slabs of 20 mm diameter and 0.5 mm thickness and swollen in PBS for 24 h prior to measurements. The gel stiffness was measured by rheology (AR 2000ex rheometer, TA Instruments, New Castle, Del.) with a 20 mm upper parallel geometry, oscillatory frequency sweep test 1-10 Hz, and 2% constant strain. Young's modulus was related to the storage modulus by the following equation:

$$E = G'2(1+v) \quad (1)$$

where E is Young's modulus and v is the Poisson's ratio which was approximated to 0.5 for polyacrylamide gels.

The device was tested in the absence of hydrogels for leakage and evaporation. To test for leakage, the device was assembled and 200 µL of colored tap water was put into each well. The device was then covered with its lid and placed at 4° C. for 48 hours. Visual observation was used at assess leakage.

To test for evaporation, the device was again assembled without hydrogels. 150 µl of 10 mM PBS were placed in three random wells in the device, the lid was placed on top and the device was left in an incubated environment at 37° C. and 5% $CO_2$ for 48 hours. The conditions were chosen to mimic standard cell culture practices. A standard 96 well plate (Thermo Scientific, Rochester, N.Y.) was used as a control. After 48 hours, the volume of fluid left in the wells was measured with a micropipette.

To test for gas exchange, the device was again assembled without hydrogels and 200 µl of complete medium (RPMI, 10% fetal bovine serum, 1% penicillin/streptomyosin, Hyclone, Logan, Utah) were placed into random wells. A standard 96-well plate was used as a control. The device was closed with the lid and placed in an incubated environment at 37° C. and 5% $CO_2$ for 48 hours. pH of the media was measured with a pH paper (pH 6.0-8.0, FischerSci; Pittsburgh, Pa.) prior to and after incubation and percent change was noted.

The evaporation rate was found to be ~10.5% per day, which was slightly higher than a standard plate for which the evaporation rate was ~9% a day (Table 1). However, the difference was not significant.

TABLE 1

Volume changes of PGS in wells of an exemplary embodiment of the device as compared to a standard 96-well plate.

| Plate Design | $V_{Initial}$ (µL) | $V_{Final}$ (µL) | % Change |
|---|---|---|---|
| Standard (96-well) | 150 | 123 ± 3.5 | 18 |
| Device | 150 | 118 ± 2.8 | 21 |

Gas exchange was tested indirectly by measuring changes in the media pH with time (Table 2). Since typical media for cell culture contains a carbonate buffer (some contain HEPES buffer which does not require $CO_2$), $CO_2$ is used to keep the pH constant—a change in $CO_2$ levels would quickly lead a change in media pH. No change in pH of the media over time was detected (similar to the control standard plate) indicating that the design allowed for proper exchange of $CO_2$.

TABLE 2 pH change of RPMI media in wells of an exemplary embodiment of the device as compared to a standard 96-well plate.

| Plate Design | Initial pH | Final pH | % Change |
|---|---|---|---|
| Standard (96-well) | ~7.3 | ~7.3 | 0 |
| Device | ~7.3 | ~7.3 | 0 |

Example 3

In this Example, cell growth, proliferation, and maintenance on the device was investigated.

Specifically, to assess the ability of the device to support cell growth and proliferation, the device was assembled with PA gels of 93.8±1.8 kPa in Young's modulus. A standard 96-well plate with PA gels of the same stiffness was used as a control. The gels in the standard 96-well plate were assembled on top of GELBOND® as described.

To compare cell viability in the device to the standard 96-well plate, $10^4$ cells/well were seeded in three random wells in the center of both plates and cultured for 72 hours. Cell metabolic activity was tested at 24 hours, 48 hours, and 72 hours with a resazurin assay. Briefly, a working solution of 50 µM resazurin sodium salt (ACROS Organics, Morris Plains, N.J.) was prepared in 10 mM PBS (pH 7.4). This was then dispensed at volumetric ratio of 1:10 resazurin:media into each well of the custom device or the standard 96-well plate where cells were seeded. The plates were incubated for 2 hours in a humidified incubator at 37° C. and 5% $CO_2$. Upon incubation 80 µl of the resazurin:media solution was transferred from each well to a well of a new 96-well plate and fluorescence was measured at excitation and emission wavelengths of 560 nm and 610 nm, respectively (SpectraMax i3, Molecular Devices, Sunnyvale, Calif.).

To compare cell morphology on the device of the present disclosure to cell morphology on a standard 96-well plate, the device and control plate were prepared as described above. Again, $10^4$ cells/well were seeded in three random wells in the center of both plates and cultured for 72 hours. At 72 hours, cells were fixed by a 10 minute exposure to ice cold ethanol, rinsed with PBS once and imaged. Cells were stained for 10 minutes with 4',6-diamidino-2-phenylindole (DAPI) and acridine orange (AO) and were then imaged with a fluorescent inverted microscope (Zeiss, Axiovert 200M), using a 10× or 20× objective.

Non-small lung cancer cell line A549 (obtained from NCI-DCTD Repository, NCI, Frederick, Md.) were cultured in RPMI 1640 medium supplemented with 10% fetal bovine serum and 1% penicillin/streptomycin and incubated in a humidified incubator at 37° C. and 5% $CO_2$. Media was changed every 48 hours. Cells were harvested by a 5 mM exposure to trypsin/EDTA and passaged every 4-5 days (at ~80% confluency).

Figure 9:
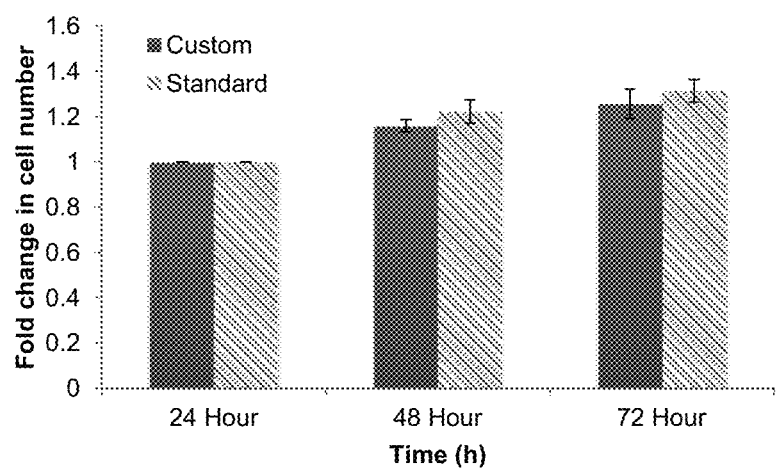
FIG. 9 is a graph depicting the fold change in cell number for A549 cells cultured in a second assembly of the system and a standard well plate for 24, 48 and 72 hours, showing no significant difference in cell number.

FIG. 9 depicts the fold change in A549 cell number as a function of culture time (up to 72 hours) as measured by a resazurin assays—an indicator of cell metabolic activity. These results demonstrated that the device was able to support cell viability and proliferation as well as a standard multiwell plate.

The cell morphology of A549 cells cultured for 24 hours on a standard 95 kPa stiffness polyacrylamide gel prepared using standard methods and a 95 kPa stiffness polyacrylamide gel prepared using the system of the present disclosure was investigated by fixing cells with formaldehyde and staining actin filaments with Alexa Fluor 546 phalloidin (to visualize actin filaments) and Hoechst 33258 (to visualize DNA in the nuclei). Cells were imaged with a fluorescent inverted microscope (Zeiss, Axiovert 200M), using a 10× or 20× objective.

Figure 10A:
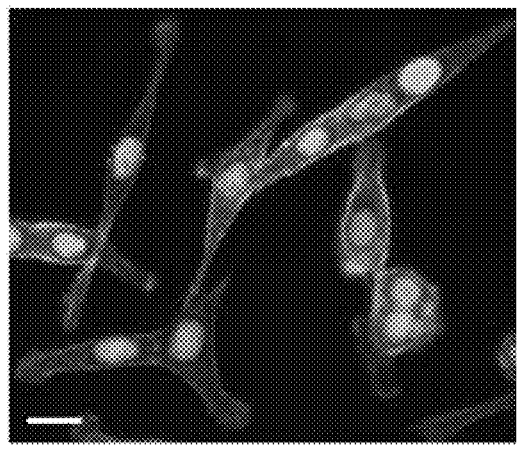
FIG. 10A is a fluorescence micrograph depicting costaining of actin filaments and nuclei of A549 cells cultured for 24 hours on a 95 kPa standard polyacrylamide hydrogel. Scale bar, 10 μm.
Figure 10B:
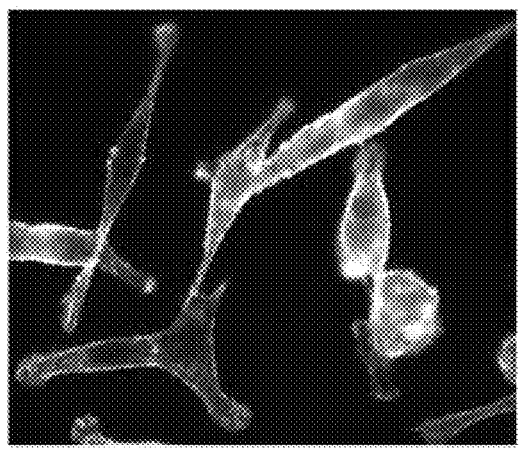
FIG. 10B is a fluorescence micrograph depicting only the actin filament staining of the A549 cells shown in FIG. 10A.
Figure 10C:
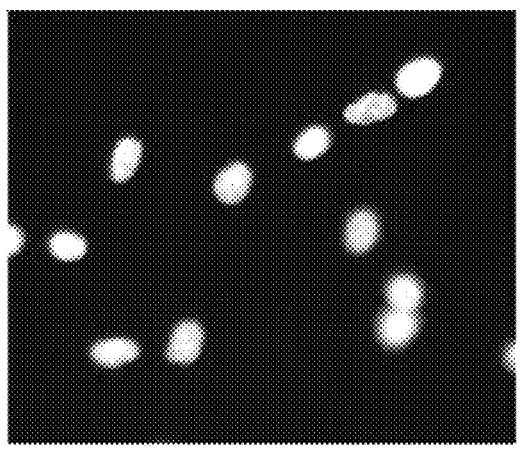
FIG. 10C is a fluorescence micrograph depicting only the nuclear staining of the A549 cells shown in FIG. 10A.
Figure 10D:
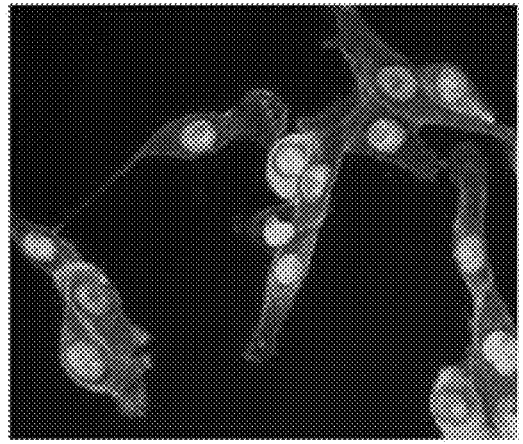
FIG. 10D is a fluorescence micrograph depicting costaining of actin filaments and nuclei of A549 cells cultured for 24 hours on a 95 kPa polyacrylamide hydrogel prepared with the system described herein.
Figure 10E:
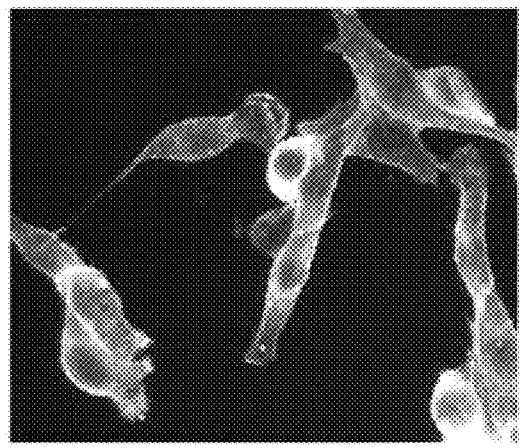
FIG. 10E is a fluorescence micrograph depicting only the actin filament staining of the A549 cells shown in FIG. 10D.
Figure 10F:
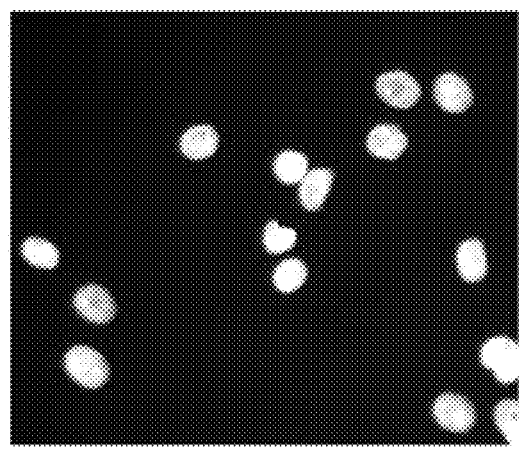
FIG. 10F is a fluorescence micrograph depicting only the nuclear staining of the A549 cells shown in FIG. 10D.

No difference in the actin of the A549 cells cultured on the standard hydrogel (FIGS. 10A-10C) as compared to the actin of the A549 cells cultured on the hydrogel prepared using the system of the present disclosure.

The custom multiwell plate design disclosed herein allows for a single-step hydrogel stiffness assay assembly that reduces preparation time and labor intensity by several fold. Hydrogel stiffness is controlled by UV intensity and exposure time to achieve a wide stiffness range from a single hydrogel precursor solution. The geometry of the individual hydrogels can be defined by a photomask and hydrogel thickness can be controlled using spacers. The multiwell plate exhibits proper gas exchange, minimum evaporation, and allows for cell growth and proliferation profiles comparable to standard multiwell plates.

What is claimed is:

1. A system for preparing a photo-patterned hydrogel-containing multiwell plate comprising:
a first assembly to prepare a plurality of photo-patterned hydrogels, the first assembly comprising:
a first base;
a flexible adhesive support in contact with the first base, the flexible adhesive support configured to receive a hydrogel precursor solution disposed thereon;
a spacer, wherein the spacer forms a border at the first base edges of the first base; and
a photomask comprising a plurality of apertures and configured to be removably positioned over the hydrogel precursor solution where upon exposure of the hydrogel precursor solution to a light source polymerizes the hydrogel precursor solution to prepare the plurality of photo-patterned hydrogels on the surface of the flexible adhesive support; and
a second assembly to prepare a multiwell plate comprising a plurality of photo-patterned hydrogels, the second assembly comprising:
an upper structure comprising a plurality of apertures configured to position each individual photo-patterned hydrogel on the surface of the flexible adhesive support within an aperture of the upper structure, wherein upon positioning each individual photo-patterned hydrogel on the surface of the flexible adhesive support within an aperture of the upper structure forms a well;
a second base; and a fastener configured to fasten the upper structure, the flexible adhesive support and the second base, wherein upon fastening the upper structure, the flexible adhesive support and the second base forms the photo-patterned hydrogel-containing multiwell plate.

2. The system of claim 1, wherein the upper structure further comprises a seal configured to seal the well formed upon assembly of the upper structure and the base.

3. The system of claim 1, wherein the upper structure further comprises a lip configured to allow for gas exchange.

4. The system of claim 1, wherein the first assembly further comprises an opaque shield configured to block the exposure of the hydrogel precursor solution to the light source.

5. A method for preparing a photo-patterned hydrogel-containing multiwell plate, the method comprising:
assembling a first assembly to prepare a plurality of photo-patterned hydrogels, the first assembly comprising:
a first base;
a flexible adhesive support in contact with the first base, the flexible adhesive support configured to receive a hydrogel precursor solution disposed thereon;
a spacer, wherein the spacer forms a border at the first base edges of the first base;
applying a hydrogel precursor solution to an upper surface of the flexible adhesive support;
positioning a photomask over the hydrogel precursor solution;
exposing the first assembly to a light source for a sufficient time to polymerize the hydrogel precursor solution exposed to the light source to prepare a flexible adhesive support comprising a plurality of photo-patterned hydrogels;
disassembling the first assembly; and
assembling a second assembly to prepare a multiwell plate comprising a plurality of photo-patterned hydrogels by positioning each individual photo-patterned hydrogel on the upper surface of the flexible adhesive support within an aperture of an upper structure wherein the upper structure comprises a plurality of apertures, wherein upon positioning each individual photo-patterned hydrogel on the surface of the flexible adhesive support within an aperture of the upper structure forms a well;
positioning an upper surface of a second base in contact with a bottom surface of the flexible adhesive support; and
fastening the base, the flexible adhesive support and the upper structure with a fastener to assemble the second assembly, wherein upon assembly of the second assembly prepares the multiwell plate comprising a plurality of photo-patterned hydrogels.

6. The method of claim 5, further comprising overlaying a portion of the photomask with an opaque shield, wherein the opaque shield blocks at least a portion of the hydrogel precursor solution from the exposure to ultraviolet light.

7. The method of claim 6, further comprising:
repositioning the opaque shield to unblock at least a second portion of the hydrogel precursor solution and
exposing to ultraviolet light the plurality of photo-patterned hydrogel and the at least a second portion of the hydrogel precursor solution, wherein the hydrogel precursor solution forms a second plurality of photo-patterned hydrogel, and
wherein the plurality of photo-patterned hydrogel comprises a first stiffness and the second plurality of photo-patterned hydrogel comprises at least a second stiffness.

8. The method of claim 5 wherein the plurality of photo-patterned hydrogel comprises a stiffness ranging from about 0.1 kPa to about 20 MPa.

9. The method of claim 5, wherein the exposure to ultraviolet light comprises from 0 to about 5 minutes.

10. The method of claim 5, further comprising contacting a cell with the plurality of photo-patterned hydrogel.

11. The method of claim 5, wherein the hydrogel precursor solution comprises a cell adhesion molecule.

12. The method of claim 5, wherein the hydrogel precursor solution comprises a biomolecule.

13. The method of claim 5, wherein the plurality of photo-patterned hydrogel further comprises an extracellular matrix protein coating.

14. A system for preparing a photo-patterned hydrogel-containing multiwell plate comprising:
a first assembly configured to prepare a plurality of photo-patterned hydrogels, the first assembly comprising:
a base configured to receive a hydrogel precursor solution disposed thereon;
a spacer, wherein the spacer forms a border at the base edges of the base; and
a photomask comprising a plurality of apertures and configured to be removably positioned over the hydrogel precursor solution where upon exposure of the hydrogel precursor solution to a light source polymerizes the hydrogel precursor solution to prepare the plurality of photo-patterned hydrogels on the surface of the base; and
a second assembly configured to prepare a multiwell plate comprising a plurality of photo-patterned hydrogels, the second assembly comprising:
an upper structure comprising a plurality of apertures configured to position each individual photo-patterned hydrogel on the surface of the base within an aperture of the upper structure, wherein upon positioning each individual photo-patterned hydrogel on the surface of the base within an aperture of the upper structure forms a well; and
a fastener configured to fasten the upper structure and the base, wherein upon fastening the upper structure and the base forms the photo-patterned hydrogel-containing multiwell plate.

15. The system of claim 14, wherein the upper structure further comprises a seal configured to seal the well formed upon assembly of the upper structure and the base.

16. The system of claim 14, wherein the upper structure further comprises a lip configured to allow for gas exchange.

17. The system of claim 14, wherein the first assembly further comprises an opaque shield configured to block the exposure of the hydrogel precursor solution to the light source.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ile Lys Val Ala Val
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Tyr Ile Gly Ser Arg
1               5